United States Patent
Rothfels

Patent Number: 5,873,818
Date of Patent: Feb. 23, 1999

[54] LARYNGOSCOPE WITH ENHANCED VIEWING CAPABILITY

[76] Inventor: Nancy Lois Rothfels, 11824 Old Eureka Way, Gold River, Calif. 95670

[21] Appl. No.: 12,405

[22] Filed: Jan. 23, 1998

Related U.S. Application Data

[60] Provisional application No. 60/036,212 Jan. 28, 1997.

[51] Int. Cl.[6] .............................. A61B 1/06; A61B 1/267
[52] U.S. Cl. ........................... 600/188; 600/189; 600/191
[58] Field of Search ................................... 600/185, 188, 600/189, 191

[56] References Cited

U.S. PATENT DOCUMENTS

| | | | |
|---|---|---|---|
| 3,005,452 | 10/1961 | Pitman | 600/188 |
| 3,771,514 | 11/1973 | Hoffman et al. | 600/188 |
| 4,086,919 | 5/1978 | Bullard | 600/188 |
| 4,306,547 | 12/1981 | Lowell | 600/188 |
| 4,320,745 | 3/1982 | Bhitiyakui et al. | 600/188 |
| 4,550,717 | 11/1985 | Berger | 600/188 |
| 4,901,708 | 2/1990 | Lee | 600/188 |
| 5,261,392 | 11/1993 | Wu | 600/188 |
| 5,263,472 | 11/1993 | Ough | 600/188 |
| 5,402,771 | 4/1995 | Pilling | 600/188 |

*Primary Examiner*—Paul J. Hirsch
*Attorney, Agent, or Firm*—George J. Netter

[57] ABSTRACT

A laryngoscope (10) with handgrip (14) and blade portion (16) has an optical system (44) secured to the blade portion with a prism lens (50) at the forward end and an eyepiece lens (48) which shifts the view toward the blade portion tip (46). A light pipe (60) directs a light beam toward the larynx to improve viewing thereof.

9 Claims, 2 Drawing Sheets

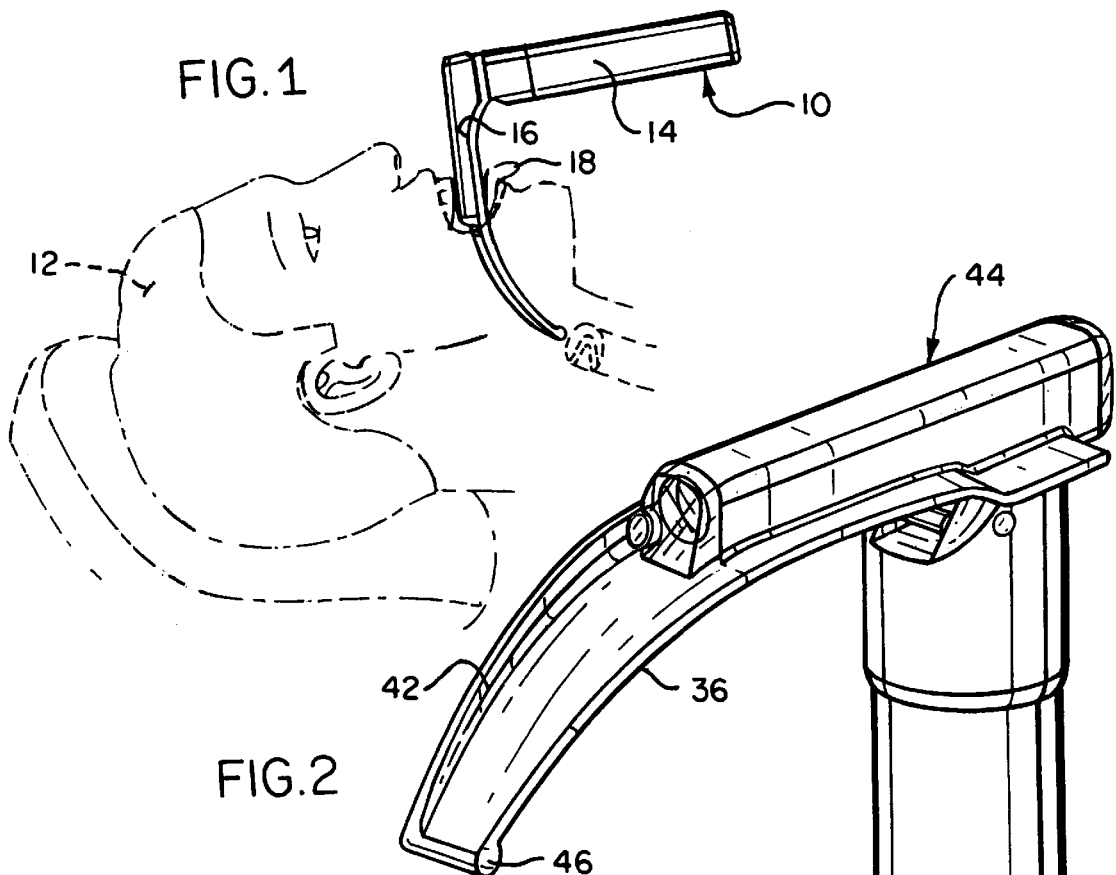
FIG.1
FIG.2
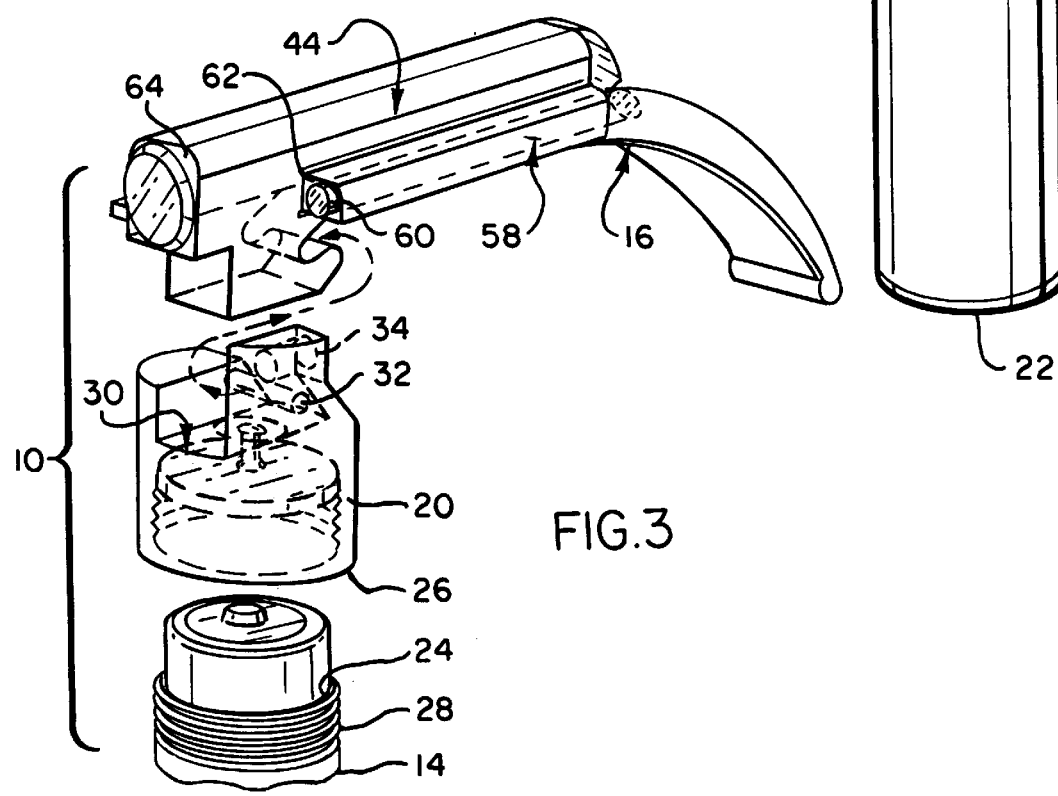
FIG.3

5,873,818

LARYNGOSCOPE WITH ENHANCED VIEWING CAPABILITY

This application claims the benefit of U.S. Provisional Application No. 60/036,212 filed Jan. 28, 1997.

BACKGROUND

1. Field of the Invention

The present invention relates generally to a laryngoscope for use by medical personnel for viewing the larynx, and, more particularly, to such a device having an expanded angular range of view.

2. Description of Related Art

As to its major parts, a laryngoscope includes a handgrip and integrally related blade portion in an overall generally L-shape arrangement. Light directed along the blade portion to aid examination typically is powered by a battery pack contained within the handgrip. In use, the blade portion is inserted into a patient's mouth lifting the tongue and mandible and removing them from obstructing the view of the larynx.

In addition to enabling visual examination of the mouth and larynx, a primary advantageous use of this instrument is to facilitate insertion of an endotracheal tube into the trachea.

A continuing difficulty in use of laryngoscopes in the past has been to obtain a satisfactory view of the larynx considering the usual space restrictions to be expected, the rather difficult viewing angle at all times, and variation in anatomical features encountered among patients.

SUMMARY OF THE INVENTION

It is, therefore, a primary aim and object of the present invention to provide a laryngoscope having an improved field of view.

In the practice of the present invention there are provided a laryngoscope with handgrip and blade portions and an optical system mounted on the blade portion providing a wide-angle field of view to one making an examination. The enlarged field of view is bent (angled) toward the outer end of the blade portion which would otherwise be out of view.

A further aspect of the invention is the provision of a light pipe mounted on the blade portion for directing a beam of light into the region of examination interest.

BRIEF DESCRIPTION OF THE DRAWING

The ensuing description of a preferred embodiment of the invention can be more particularly understood by those skilled in the appertaining arts on making reference to the following description with further reference to the accompanying drawing in which:

FIG. 1 is a schematic depiction of a laryngoscope being used to view a patient's larynx;

FIG. 2 is a perspective view of a laryngoscope of the present invention;

FIG. 3 is a partially fragmentary, exploded view of the invention of FIG. 2;

DESCRIPTION OF A PREFERRED EMBODIMENT

Figure 4:
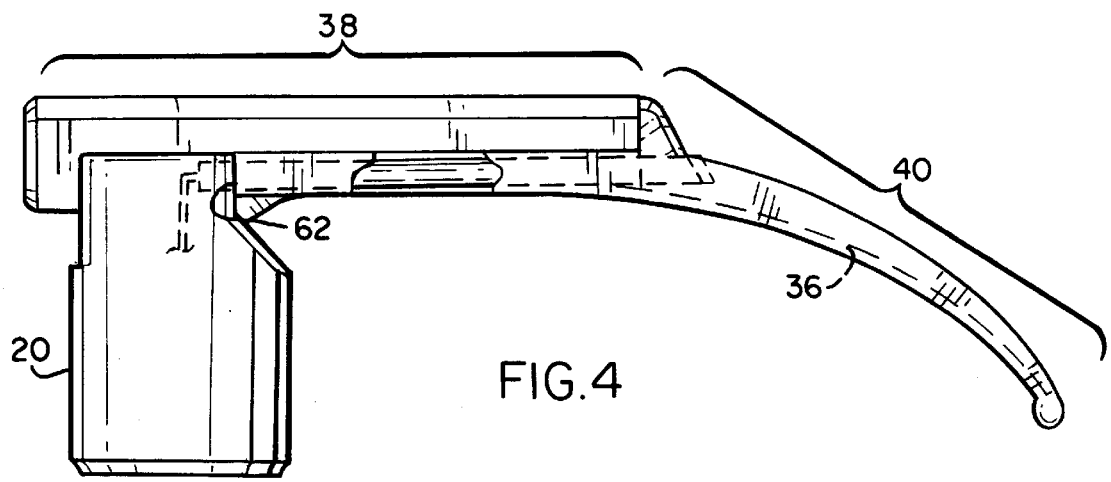
FIG. 4 is an elevational view.
Figure 5:
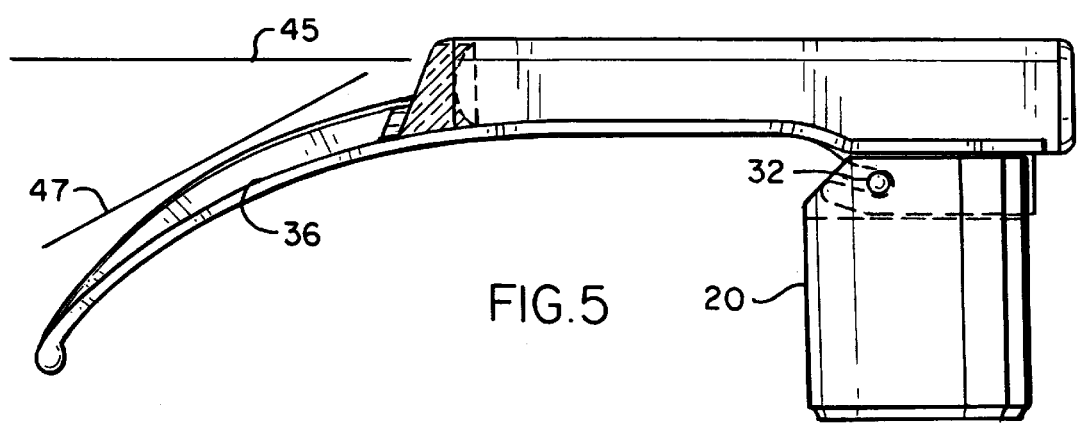
FIG. 5 is a further elevational view taken from the side opposite that of FIG. 4.

Turning now to the drawing and particularly FIG. 1, there is shown the laryngoscope instrument of the present invention enumerated as 10 placed in the mouth of a patient 12 for viewing the larynx 13 and to aid in the insertion of an endotracheal tube. The instrument includes a handle or handgrip 14 and a blade portion 16, the latter being used to lift the tongue and mandible 18. Also, on occasion the blade portion is levered on the front teeth of the patient in order to see the larynx.

With reference now particularly to FIGS. 2 and 3, the instrument 10 is seen to specifically include three separable parts, namely, the handle 14, blade portion 16 and a handle cap 20. As will be more specifically described, these different parts can be readily assembled together for use.

The handle 14 is essentially a hollow tube having a closed lower or outer end 22 and an open upper end 24. One or several dry cell batteries (not shown) are typically located within the handle cavity to provide power for an examination light to be described.

The cap 20 is a hollow cylindrical member with one end 26 open and containing internal threads for mating with threads 28 plus a washer or O-ring (not shown) to sealingly close off the handle open end 24. The upper or closed end of the cap has a parallel-sided slot 30 with a securement pin 32 having its ends affixed to the parallel sides and spaced from the slot bottom. A light source shown schematically at 34 is automatically interconnected with the battery power source in the handle upon full assembly of instrument. The securement technique between the handle, cap and blade portion can be identical to that disclosed in U.S. Pat. No. 5,501,651. FLUID SUBMERSIBLE LARYNGOSCOPE PREVENTING ELECTROLYTIC CURRENT FLOW.

The blade portion 16 as seen in elevation (FIGS. 2–5) includes an elongated flat base 36 which has a substantially straight part 38 adjacent where it is connected to the cap 20 and an integral part 40 which curves generally toward the handle. A stiffening sidewall 42 extends along one lateral edge of the base. Overall blade surface features and shape for accomplishing tongue and mandible elevation during examination of a patient can be the same as disclosed in the U.S. Pat. No. 5,501,651.

A primary contribution of this invention is the addition of an optical system 44 to the blade portion 16 which provides a wider angle of view to the one making an examination than is possible by taking an otherwise unassisted view along the blade. More particularly, the system 44 provides a view that extends beyond and just above the outer end 46 of the blade portion. As can be best seen in FIG. 5, the normal line of sight 45 (i.e., unassisted by optics) is considerably higher than desired for viewing the larynx. On the other hand, with the described optics the new line of sight 47 is directed downwardly substantially from the normal line 45, and therefore, requires at most a very minor physical shifting of the instrument to have a satisfactory view of the larynx.

Figure 6:
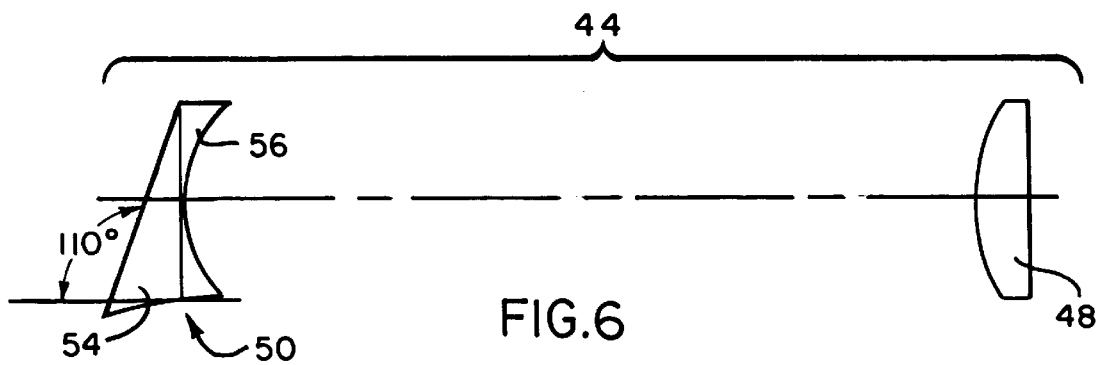
FIG. 6 is a schematic representation of an optical system for use in the invention.

For the ensuing detailed description of the optical system 44, reference is made to FIG. 6. The system includes a plano-convex eyepiece lens 48 which as the name implies is located at a point that can be conveniently accommodated to the eye of a user of the instrument preferably at a point just rearwardly of the handle 14. A prism-lens 50 serves as the forwardmost optic in the system located approximately at the point of demarcation between the flat base straight part 38 and curved part 40. The front face of the prism slopes rearwardly from bottom to top at a total angle of 110 degrees.

A hollow tube 52 affixed to the blade portion base 36 has the eyepiece lens 48 received in one end and the prism-lens 50 in the other end. The tube 52 may be separately constructed and suitably secured to the base 36. Alternatively, the tube and base 36 may be constructed unitarily from metal or plastic (e.g., injection molding).

In a practical construction of an optical system 44 for the present invention, the eyepiece was constructed of optical quality acrylic having a smooth flat surface facing the user's eye and an opposite surface having a radius of 54.3337 mm providing a focal length of +110 mm. The prism-lens 50 was constructed of optical grade acrylic and consisted of a prism optic 54 cemented to a further lens 56 having a concave surface with a radius of 12.3555 mm facing the eyepiece. Prism optic 54 and lens 56 when assembled together (or optionally molded in one piece) provide a smooth sloping prism face of 110 degrees to the system axis, and has a focal length of −25 mm for the prism/lens combination. The prism and lenses may be optionally made of glass, or a number of transparent plastics, e.g., polycarbonate, acrylic, or crystalline polystyrene.

With respect to the functional operation of the optical system 44, the concave portion of lens 56 serves to produce a wide-angle view, while the companion prism lens 54 directs the view toward the blade tip 46 to better expose the larynx. Also, the lens 56 "miniaturizes" objects view, while the eyepiece lens 48 compensates for the miniaturization as well as providing for focusing.

A further aspect of the present invention is the provision of a light direction means 58 which extends from the light source 34 along a path generally parallel to the optical axis of the optical system 44 and closely spaced thereto (FIGS. 3 and 4). Specifically, the direction means includes a light pipe 60 consisting preferably of a cylindrical rod of a good light transmitting material (e.g., optical quality acrylic). The light pipe is located within a tubular housing 62 which can be secured to the optical system housing 64, or, alternatively, the two housings can be unitarily constructed with the blade base 36. The forward end 64 of the light pipe is preferably located forwardly of the prism 54 so as not produce any undesirable glare in the optical system. Moreover, the forward end face 64 is sanded or etched to produce diffused light which reduces glare or undesirable back reflection.

In accordance with the present invention there is provided laryngoscopic apparatus which overcomes certain prior existing deficiencies in such equipment, especially viewing difficulties encountered when the apparatus is being used in connection with insertion of an endotracheal tube into a trachea. The described apparatus achieves a highly expanded viewing region and bends or angles the line of sight toward the outer end of the blade; thereby approximating a direct line of sight view of the larynx and trachea.

Although the present invention is described herein in connection with a preferred embodiment, it is to be understood that those skilled in the appertaining arts may contemplate changes that come within the spirit of the invention as described and within the ambit of the appended claims.

What is claimed is:

1. In laryngoscope apparatus having a handle and unitarily related blade portion, the improvement comprising:

an optical system mounted to the blade portion including an eyepiece;

a prism lens spaced forwardly from said eyepiece along a straightline optical axis providing visual examination of the trachea and adjacent tissue lying beyond the range of normal visibility of an observer viewing directly along the optical axis, said prism lens having a surface facing forwardly in the direction of an object of interest, which surface is flat and canted at an angle different from 90 degrees to the optical axis; and a further lens located between the prism lens and eyepiece with a concave lens surface facing said eyepiece.

2. Laryngoscope apparatus as in claim 1, in which there are further provided a light source, a light pipe having a first end in light receiving relation to said light source and a second and positioned to direct light received from said light source generally toward an outer end of the blade portion.

3. Laryngoscope apparatus as in claim 2, in which the light pipe second end has a light diffusing surface.

4. Laryngoscope apparatus as in claim 2, in which the light pipe second end is located forwardly of the prism lens closer to the outer end of the blade portion.

5. Laryngoscope apparatus as in claim 2, in which the light pipe includes a hollow housing with open ends and a rod constructed of a good light transmitting material.

6. Laryngoscope apparatus as in claim 5, in which the rod material is acrylic.

7. Laryngoscope apparatus, comprising:

a blade portion having a generally straightline part and a curved part integral therewith;

a handle affixed to the straightline part of the blade portion and including a light source;

housing means affixed to the blade portion having first and second elongated cavities extending along the straightline part generally parallel to one another;

an eyepiece lens including a plano-convex lens and a prism lens arranged in the housing means first cavity in spaced apart relation, said prism lens having a forward facing flat surface canted at an angle of approximately 110 degrees to the straightline part of the blade portion, a back surface, and a further lens adhered to the prism back surface having a concave surface facing the eyepiece lens; and a light pipe received in the second cavity having a first end in light receiving relation to the light source and a second end located outwardly beyond the prism lens.

8. Laryngoscope apparatus as in claim 7, in which the light pipe includes a length of a good light transmitting material the second end of which has a light diffusing surface.

9. Laryngoscope apparatus as in claim 7, in which the light pipe second end includes a flat end surface canted with respect to the light pipe axis.

* * * * *